United States Patent [19]
Bloor

[11] Patent Number: 6,166,084
[45] Date of Patent: Dec. 26, 2000

[54] COMPOSITIONS FOR THE TREATMENT OF CHRONIC WOUNDS

[75] Inventor: Stephen Bloor, Preston, United Kingdom

[73] Assignee: Johnson & Johnson Medical, Ltd., Edinburgh, United Kingdom

[21] Appl. No.: 08/992,649

[22] Filed: Dec. 17, 1997

[51] Int. Cl.$^7$ .................................................. A61K 31/16
[52] U.S. Cl. ........................... 514/613; 514/616; 514/928
[58] Field of Search ..................................... 514/562, 613, 514/616, 928

[56] References Cited

U.S. PATENT DOCUMENTS

| | | |
|---|---|---|
| 3,749,770 | 7/1973 | Martin . |
| 4,276,284 | 6/1981 | Brown . |
| 4,414,387 | 11/1983 | Broggi et al. . |
| 4,476,120 | 10/1984 | Gonella . |
| 4,567,163 | 1/1986 | Ponchiroli . |
| 4,708,965 | 11/1987 | Morgan . |
| 4,724,239 | 2/1988 | Morgan . |

FOREIGN PATENT DOCUMENTS

| | | |
|---|---|---|
| 0 300 100 | 1/1989 | European Pat. Off. . |
| 0300100 | 1/1989 | European Pat. Off. . |
| 2092822 | 1/1972 | France . |
| 1154914 | 6/1969 | United Kingdom . |
| 2 177 919 | 2/1987 | United Kingdom . |
| WO 91/02538 | 3/1991 | WIPO . |
| WO91/02538 | 3/1991 | WIPO . |
| WO 95/05852 | 8/1994 | WIPO . |
| WO 95/00136 | 1/1995 | WIPO . |

OTHER PUBLICATIONS

Joao Batista Viana et al. Observacoes Preliminares Sobre a Aplicacao Da N–Acetil–L–Cisteina Nas Ulceras Cronicas Das Pernas. Rev. Med. Bras., vol. 29, No. 4, 1972, pp. 201–205, XP000606606.

Clinical and Experimental Dermatology 1992; 17:427–432, A.S.Salim University Department of Surgery at the Medical City, Baghdad, Iraq, Role of Sulphydryl–Containing Agents in the Management of Venous(Varicose) Ulceration. A New Approach.

World Journal of Surgery 15, 264–269, 1991, Aws S. Salim, Ph.D.(Surg.), F.R.C.S.Ed., F.R.C.S. Glasg., F.I.C.S., F.C.I.C.D., University Dept of Surgery, The Medical City, Baghdad, Iraq, Original Scientific Reports. The Role of Oxygen–Derived Free Radicals in the Management of Venous (Varicose) Ulceration: A New Approach.

Annales Pharmaceutiques Francaises, vol. 35, No. 9–10, 1977, A Quevauviller & L Vu Ngoc Huygen "Treatment of Cutaneous Burns Provoked by Hydrofluoric Acid in the Rat", pp. 365–370.

Journal of Investigative Dermatology, vol. 102, No. 6, 1994, G. Senaldi et al. "Protective Effect of N–Acetylcysteine in Hapten Induced Irritant and Contact Hypersensitivity Reactions:, pp. 934–937.

*Primary Examiner*—Rebecca Cook
*Attorney, Agent, or Firm*—Andrew C. Farmer; Theodore J. Shatynski

[57] ABSTRACT

The present invention provides the use of N-acetyl cysteine and its pharmaceutically acceptable salts and derivatives, for the preparation of a composition for treatment or prophylaxis of chronic ulcers. In particular, the treatment of venous ulcers, diabetic ulcers and decubitis ulcers.

20 Claims, 2 Drawing Sheets

COMPOSITIONS FOR THE TREATMENT OF CHRONIC WOUNDS

The present invention relates to compositions for the treatment and prophylaxis of chronic wounds such as venous ulcers, diabetic ulcers and pressure sores (decubitis ulcers).

Currently preferred procedures for the treatment of chronic wounds, and in particular venous ulcers, diabetic ulcers and pressure sores include absorbent wound dressings, such as the following: Actisorb (Registered Trade Mark of Johnson & Johnson), which is an odour absorbing dressing; Bioclusive (Registered Trade Mark of Johnson & Johnson) which is a semi-permeable film dressing for pressure sores and minor burns; N-A Dressing (Registered Trade Mark of Johnson & Johnson), which is a non-adherent wound contact dressing for ulcerative wounds; Fibracol (Registered Trade Mark of Johnson & Johnson), which is a collagen alginate composite dressing; Tielle (Registered Trade Mark of Johnson & Johnson), which is intended for light to medium exuding wounds; Granuflex (Registered Trade Mark of Convatec), for exuding leg ulcers and pressure sores; Compression bandages for venous ulcers; and Kaltostat (Registered Trade Mark of Convatec), which is an alginate dressing for leg ulcers, pressure sores and other wounds.

Current treatments also include simple medicated wound dressings, such as the following: Inadine (Registered Trade Mark of Johnson & Johnson), which is a slow release povidone iodine non-adherent dressing; Flamazine (Registered Trade Mark of Smith & Nephew), which is a 1% silver sulphadiazine product for the treatment of infected wounds or ulcers; Aserbine (Registered Trade Mark of Forley), which is a desloughing agent for ulcers and pressure sores; Betadine (Registered Trade Mark of Seton), which is a Povidone iodine ointment for decubitus and venous stasis ulcers; and Varidase (Registered Trade Mark of Lederle), which is a debriding agent containing streptokinase and streptodornase.

Current or prospective treatments also include therapeutic pharmaceutical compositions, including: Iamin (R) (Registered Trade Mark of ProCyte Corporation), which is a copper-peptide product; and Procuren (Registered Trade Mark of Curative Technologies), which is a natural platelet-derived wound healing composition.

N-acetyl cysteine (N-acetyl-3-mercaptoalanine hereinafter referred to as NAC) is a derivative of the naturally occurring amino acid N-cysteine. NAC is a sulfhydryl group donor and is therefore considered an antioxidant, and as such it is commonly used as a stabilizer compound on pharmaceutical preparations. NAC is also available in pharmaceutical compositions for the treatment of certain medical conditions, as follows.

A first medical use of NAC is for the treatment of paracetamol (acetaminophen) overdose. The administered NAC acts as a sulfhydryl group donor to restore natural glutathione levels, and may also act as an alternative substrate for toxins, thus protecting the liver against damage due to paracetamol overdose. NAC compositions for this application are available under the Registered Trade Mark PARVOLEX from Evans Medical Limited, UK.

NAC has mucolytic properties, i.e. it reduces the viscosity and tenacity of mucous secretions. This property has been used in eye drops for the relief of dry eye syndromes, for example the eye drops produced under the Registered Trade Mark ILUBE by CUSI (UK) Limited. Similarly, the mucolytic properties of NAC have been used to treat acute chronic bronchitis and viscous mucous secretions associated with cystic fibrosis, for example under the Registered Trade Mark FABROL (Zyma Healthcare, UK).

WO95/00136 describes the use of NAC or pharmaceutically acceptable salts or derivatives thereof for the topical or systemic treatment of hyperkeratosis or disorders mediated by proteinases. The specific diseases mediated by proteinases cited in this application are lichen planus, bullous diseases and mouth ulcers.

WO93/04669 describes the use of NAC and its derivatives for regulating skin wrinkles and/or skin atrophy,.

U.S. Pat. No. 4,708,965 describes the use of NAC and its derivatives for the treatment of herpes eruptions and ulcers. This use is based on the ability of NAC to interfere with leukotriene synthesis.

U.S. Pat. No. 4,724,239 describes treatment of chemical ulcers caused by leukotriene production, the treatment being effected with compositions containing NAC.

It has now been found that NAC is highly effective for the treatment or prophylaxis of chronic wounds, in particular the group of chronic ulcers consisting of venous ulcers, diabetic ulcers and pressure sores (decubitis ulcers).

Accordingly, the present invention provides the use of a N-acetyl cysteine or a pharmaceutically acceptable salt or derivative thereof for the preparation of a composition for the treatment or prophylaxis of chronic wounds. Preferably, the chronic wounds are selected from the group consisting of venous ulcers, diabetic ulcers and pressure sores (decubitis ulcers).

The compositions containing N-acetyl cysteine or the pharmaceutically acceptable salt or derivative thereof may be suitable for local or systemic, oral or parenteral administration. However, preferably, the compositions is in the form of an ointment for topical administration to the chronic ulcer. Preferably, the ointment comprises from 0.001% to 10% w/v, more preferably 0.01% to 1% w/v, of the N-acetyl cysteine, or a salt or derivative thereof, in a pharmaceutically acceptable carrier. Suitable carriers include: Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also including creams/ointments used for topical pharmaceutical preparations, e.g. creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilisers such as EDTA.

In alternative preferred embodiments, the composition is in the form of a solid ulcer dressing having the N-acetyl cysteine dispersed therein or thereon. For example, the wound dressing may be a woven, nonwoven or knitted fabric having the N-acetyl cysteine coated thereon, or it may be a bioresorbable polymer film or sponge having the N-acetyl cysteine dispersed therein for sustained release at the ulcer site.

Where the NAC is used for prophylaxis of chronic wounds, conventional transdermal pharmaceutical forms may be appropriate, such as slow-release skin patches to prevent or minimise ulcer formation or breakout. More conventional systemic administration, such as oral or parenteral administration, may be preferable.

Without wishing to be bound by any theory, it is thought that the NAC promotes healing or prophylaxis of chronic ulcers by regulating matrix metalloproteinases (MMP's) at the ulcer site. It is thought that the balance between proteolytic enzymes and their inhibitors is critical to the persistence and healing of chronic ulcers, and that the NAC corrects this balance in chronic ulcers.

In addition, the NAC may influence chronic ulcers through the following mechanisms. Firstly, by inhibition of tumour necrosis factor (TNF) mediated effects. NAC has the potential to inhibit the effects of TNF by interfering with the intracellular signalling resulting from the TNF receptor activation. Secondly, NAC can also neutralise potentially harmful oxygen radicals, which in turn can induce the expression of MMP's and other molecules. Thirdly, NAC has the potential to inhibit the influx of inflammatory cells to a wound site by inhibiting the transcription of genes for adhesion molecules such as ICAM-1 and other adhesion molecules on inflammatory cells and endothelial cells. It can do this by inhibiting the activation of nuclear transcription factors such as $NF_k$-B, which controls the transcription of the MMP-9 gene, adhesion molecule genes such as ICAM-1 and inflammatory mediator genes such as TNF-α. Finally, NAC can interfere with the inflammatory mediators such as leukotrienes.

It will be appreciated that a number of salts and derivatives of N-acetyl cysteine will exhibit the same healing effect on chronic ulcers as N-acetyl cysteine itself. In particular, salts of N-acetyl cysteine with inorganic cations such as sodium, alkyl ammonium cations, and other pharmaceutically acceptable cations are preferred. Additionally, a number of esters and thioesters of NAC can function as prodrugs, undergoing hydrolysis to NAC in vivo.

Other preferred derivatives of N-acetyl cysteine are its esters, thioesters and thioethers. In some preferred embodiments, both the thiol group and the carboxylate group of the N-acetyl cysteine may be derivatized. In yet other active derivatives, the acetyl group of N-acetyl cysteine may be replaced by another acyl group. Preferred derivative of NAC represented by the following formula or pharmaceutically acceptable salts or derivatives thereof:

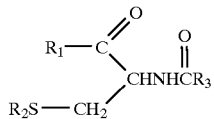

wherein:
$R_1$ is H, optionally substituted $C_1$–$C_{10}$ alkyl, optionally substituted $C_6$–$C_{14}$ aryl, or an inorganic, alkyl ammonium or protonated amino acid cation;

$R_2$ is H, optionally substituted $C_1$–$C_{10}$ alkyl, optionally substituted $C_6$–$C_{14}$, aryl, optionally substituted —C (O or S) $C_6$–$C_{14}$ alkyl, optionally substituted —C (O or S) $C_6$–$C_{14}$ aryl, or $R_2$ together with the sulfur to which it is attached form a thioester of a saturated or unsaturated fatty acid, lactic acid, retinoic acid or ascorbic acid; and $R_3$ is optionally substituted $C_1$–$C_{10}$ alkyl or optionally substituted $C_6$–$C_{14}$ aryl.

A particularly preferred derivative is glutathione (glutamyl cysteinyl glycine).

Specific embodiments of the present invention will now be described further, together with examples of the use thereof, with reference to the accompanying drawings.

EXAMPLE 1

Figure 1:
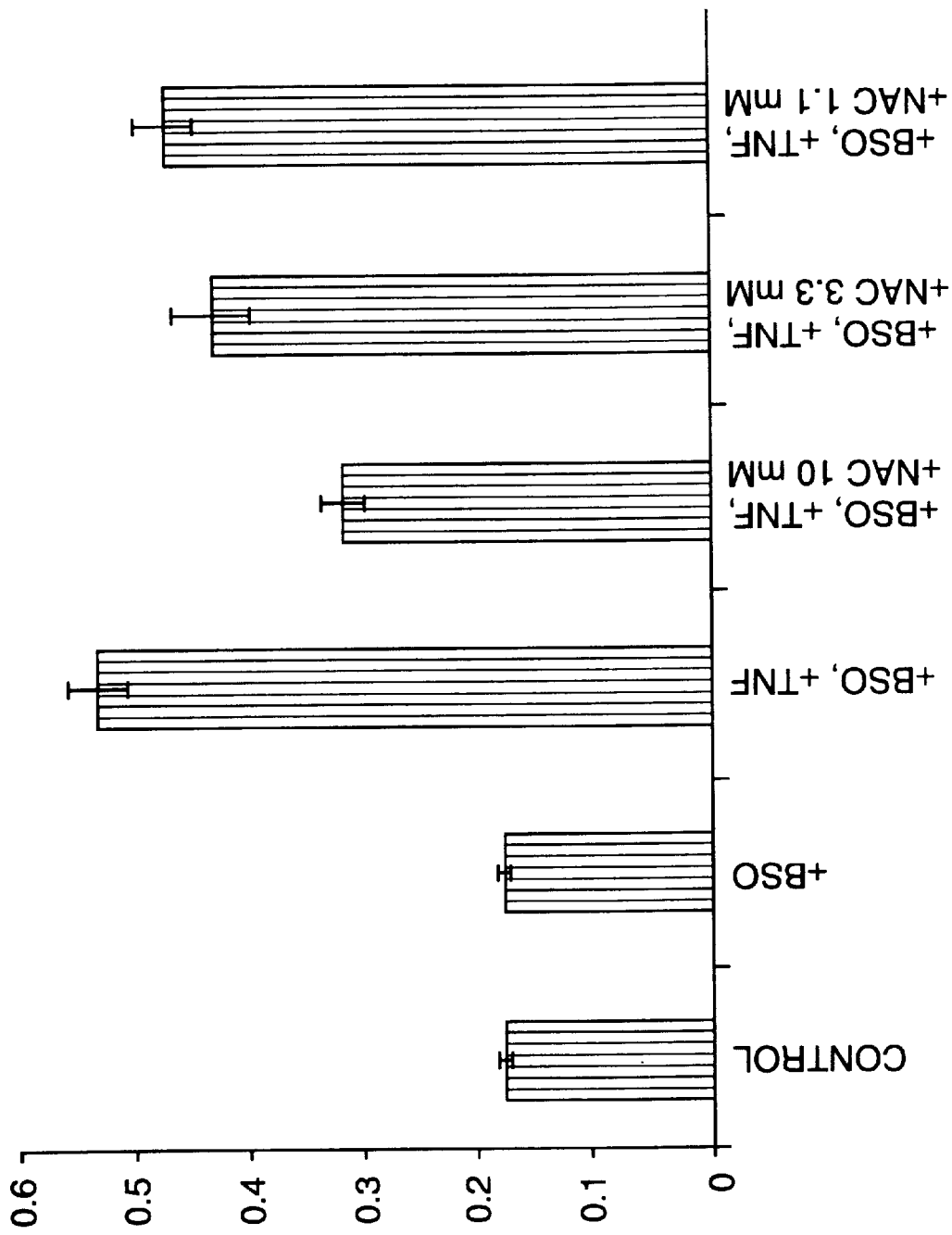
FIG. 1 shows a bar chart of the level at TNF-α induced expression of ICAM-1 by HUVEC for the six different experimental systems described in Procedure 1 below.

A topical formulation for the delivery of NAC is prepared as follows (percentages are by weight, based on the total weight of the formulation):

| | |
|---|---|
| Carboxymethyl Cellulose | 2.4% |
| Hydroxyethyl Cellulose | 0.28% |
| Sodium Chloride | 0.24% |
| Propylene Glycol | 20.24% |
| N-Acetyl Cysteine | 1.63% |
| Water | 75.21% |

This formulation contains NAC at a concentration of 100 mm, and is suitable for application directly to the surface of a chronic ulcer.

Procedure 1

The effects of NAC on the expression of the TNF-α induced CD 54, Intercellular Adhesion Molecule (ICAM-1) by Human Umbilical Vein Endothelial Cells (HUVEC) was assessed as follows.

DL-Buthionine sulphoximine (BSO) was used to pretreat the cells. BSO is an inhibitor of glutathione synthesis and therefore reduces the glutathione content of the HUVEC rendering them more susceptible to oxidative stress and mimicking the conditions implicated in chronic wounds. NAC was used as a treatment to inhibit the expression of ICAM-1 by interfering with the TNF-α mediated intracellular signalling.

HUVEC were seeded to wells of 96 well plates (5000 cells per well in 100 μl Endothelial Growth Medium (EGM)). The plates were allowed to grow until the cells reached 90% confluence. The medium was decanted from each plate and the following treatments (all volumes were 200 μl, performed in quadruplicate wells) where then applied to the HUVEC. The contents of each well were decanted prior to the addition of the treatments for the second (18 hours) time period.

1. Serum free EGM (EBM) alone for 24 hours, followed by EBM alone for 18 hours.
2. BSO (50 μM) in EBM for 24 hours, followed by EMB alone for 18 hours.
3. BSO (50 μM) in EBM for 24 hours, followed by Tumour Necrosis Factor-α(0.5 $ngml^{-1}$) in EBM for 18 hours.
4. BSO (50 μM) plus N-acetyl cysteine (NAC, 10 mM) in EBM for 24 hours, followed by N-acetyl cysteine (NAC, 10 mM) plus TNF-α(0.5ng/ml) in EBM for 18 hours.
5. BSO (50 mM) plus N-acetyl cysteine (NAC, 3.3 mM) in EBM for 24 hours, followed by N-acetyl cysteine (NAC, 10 mM) plus TNF-α(0.5 ng/ml) in EBM for 18 hours.
6. BSO (50 μM) plus N-acetyl cysteine (NAC, 1.1 mM) in EBM for 24 hours, followed by N-acetyl cysteine (NAC, 10 mM) plus TNF-α(0.5 $ngml^{-1}$) in EBM for 18 hours.

ICAM-1 expression, stimulated by inflammatory mediators such as tumour necrosis factor, can be detected on the surface of cells (endothelial cells, monocytes, T&B cells, keratinocytes, chondrocytes and epithelial cells) using ELISA techniques, as follows:

1. Remove the liquid from the plates by inverting and tapping the plates. Fix the cell monolayer with 70% ethanol (100 μl) for 10 minutes.
2. Wash plates once with cell culture medium +10% Fetal Calf Serum (FCS) (200 μl).
3. Add anti-ICAM-1 antibody (Boehringer catalog no. 1428543) Prepared as a 2 μg/l solution in PBS +1% BSA immediately prior to use (100 μl per well) and incubate for 1 hour at 37° C.
4. Remove antibody solution by inverting and tapping the plates. Wash plates with PBS +1% BSA (200 μl per well, three times).
5. Add Goat anti-Mouse peroxidase linked antibody (Sigma A-4416) prepared at 1:1000 dilution in PBS +1% BSA (100 μl per well) and incubate for 1 hour at 37° C.
6. Remove antibody solution by inverting and tapping the plates. Wash plates with PBS and +1% BSA (200 μl per well, three times).
7. Add substrate solution (100 μl per well). The substrate solution is TMB ELISA substrate from Sigma Chemical Co. Leave plate at room temperature for colour development (maximum 30 minutes).
8. Stop the reaction when colour develops by the addition of 1M $H_2SO_4$ (100 μl per well) and read the absorbance at 450 nm using a Dynatech (RTM) plate reader.

The results, shown in FIG. 1, illustrate a concentration-dependent inhibition of ICAM-1 expression by NAC. All NAC concentrations show a significant inhibition of ICAM-1 expression (P<0.05, Students T-test).

Procedure 2

The effect of NAC concentration on the activity of matrix metalloproteinases (MMP) from human wound fluid was assessed as follows.

The MMP activity was determined by gelatin SDS polyacrylamide gel electrophoresis (zymography) similar to that described by Heussen C. and Dowdle E. B. in *Anal. Biochem.* 102:196–202 (1980).

The experimental method was as follows:
1. Gel preparation. The following components were mixed thoroughly:
   1. 5 ml 30% acrylamide/bis acrylamide (30 g acrylamide (Sigma A8887) plus 0.8 g N-N'-methylene bis-acrylamide (Sigma M7279) in 100 ml deionised water).
   2. 6.05 ml deionised water.
   3. 3.75 ml 1.5M Tris-HCl buffer.
   4. 150 μl 10% sodium dodecyl sulphate (SDS. Fisons S/5200/53).
   5. 1 ml warm (60° C.) gelatin (Sigma G9382) solution (7.5 mgml$^{-1}$).
   6. Immediately prior to casting the gel 50 μl 10% ammonium persulphate (APS, Fisons A/6160/53) and 12.5 μl tetramethylethylenediamine (TEMED, Sigma T9281).
      4.5 ml of the above mixture was added to the electrophoresis apparatus (Dual Mini Slab Kit, Atto Corporation), and covered with propanol saturated water. The gel was left gel to polymerise for at least 45 minutes. Then propanol solution was decanted and added to 1 ml of stacking gel solution (3.15 ml deionised water, 0.75 ml 30% acrylamide/bis-acrylamide, 12.5 ml 1.5M Tris-HCl, 50 μl 10% SDS, 50 μl ammonium persulphate and 10 μl TEMED). Finally, a sample comb (8 lane comb) was inserted and the gel left to polymerise for at least 45 minutes.
2. Sample preparation: A matrix metalloprotease (MMP) sample (10% solution of human acute wound fluid diluted in MMP proteolysis buffer (see below)) was diluted 1:1 with sample buffer (6.3 ml 0.5M Tris-HCl pH 6.8, 2.5 ml glycerol, 0.5 g SDS, 16.2 ml deionised water and bromophenol blue to colour).
3. Sample loading and electrophoresis: 20 μl of the MMP samples were loaded into 8 lanes of the gel. The MMP's were separated for 1 hour at 20 mA/100V per gel until the dye front was almost at the bottom of the gel. The gel apparatus was then dismantled and the gel removed.
4. Proteolysis: Washed gels for 30 minutes with 100 ml 2.5% Triton X-100. The procedure was repeated three times. The gels were cut into slices consisting of two lanes per slice. The gel slices were incubated in 20 ml proteolysis buffer (50 mM Tris-HCl pH 7.8, 50 mM $CaCl_2$, 0.5M NaCl) containing the following treatments (each treatment was adjusted to pH 7.8) for 18 hours at 37° C.: (1) proteolysis buffer alone; (2) N-acetyl cysteine (44 mM); (3) N-acetyl cysteine (4.4 mM); (4) N-acetyl cysteine (0.44 mM).
5. Gel development: The gels were washed with deionised water and stained with 0.1% Coomassie blue R250 in 10% acetic acid, 40% methanol and 50% deionised water for 1 hour. The gels were then destained with 7.5% acetic acid, 10% methanol and 82.5% deionised water until zones of proteolysis had resolved in the controls (MMP sample incubated in proteolysis buffer alone).

The area of the individual zones of clearance on the gels, which are due to proteinase activity, were accurately measured by the Optilab (RTM) system. This was achieved by repeating each experiment (n=2).

Figure 2:
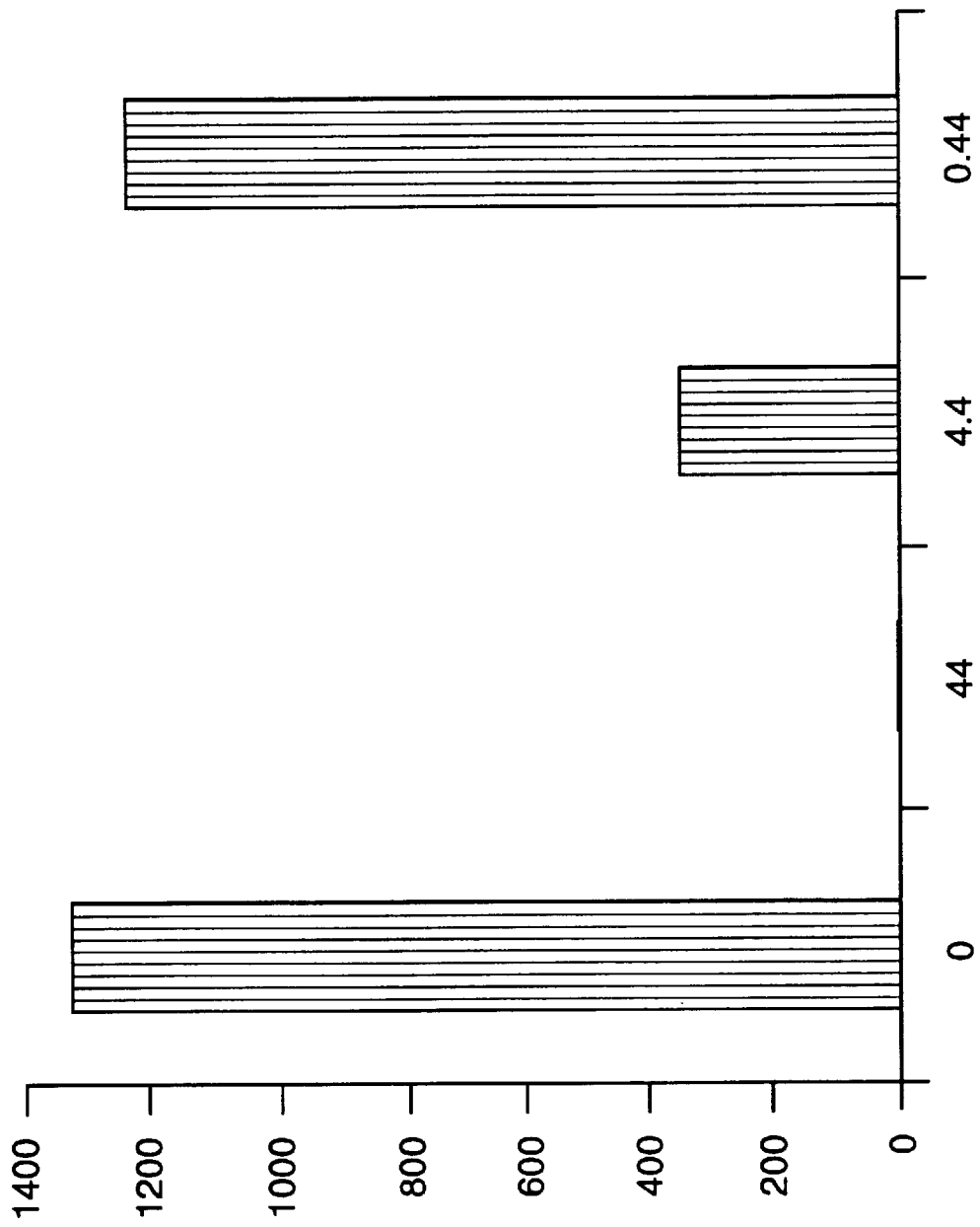
FIG. 2 shows a bar chart of matrix metalloproteinase (MMP) activity in arbitrary units in the presence of 0 (control), 0.4 mM, 4.4 mM and 44 mM concentration of NAC.

The results, shown in FIG. 2, demonstrate a clear concentration-dependent inhibition of MMP activity with NAC concentration. The inhibition of MMP activity is substantially complete in 44 mM NAC solution. Approximately 70% inhibition is observed in 4.4 mM NAC solution, and approximately 10% inhibition in 0.44 mM NAC.

What is claimed is:

1. A method for the treatment or prophylaxis of a chronic wound in a mammal, the chronic wound being selected from the group consisting of venous ulcers, diabetic ulcers, and pressure sores, the method comprising the step of topically applying to the chronic wound an effective amount of a composition comprising a compound of the formula:

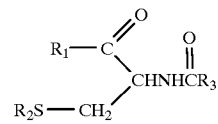

wherein:
$R_1$ is H, $C_1$–$C_{10}$ alkyl, $C_6$–$C_{14}$ aryl, or an inorganic, alkyl ammonium or protonated amino acid cation;
$R_2$ is H, $C_1$–$C_{10}$ alkyl, $C_6$–$C_{14}$, aryl optionally substituted —C O $C_6$–$C_{14}$ alkyl, optionally substituted —C S $C_6$–$C_{14}$ alkyl, optionally substituted —C O $C_6$–$C_{14}$ aryl, optionally substituted —C S $C_6$–$C_{14}$ aryl, or $R_2$ together with the sulfur to which it is attached form a thioester of a saturated or unsaturated fatty acid, lactic acid, retinoic acid or ascorbic acid; and
$R_3$ is H, $C_1$–$C_{10}$ alkyl or $C_6$–$C_{14}$ aryl;
or a pharmaceutically acceptable salt thereof; thereby inhibiting matrix metalloproteinases in said chronic wound.

2. A method for the treatment or prophylaxis of a chronic wound in a mammal, the chronic wound being selected from the group consisting of venous ulcers, diabetic ulcers, and pressure sores, the method comprising the step of systemically administering an effective amount of a composition comprising a compound of the formula:

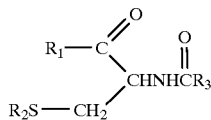

wherein:

R₁ is H, $C_1$–$C_{10}$ alkyl, $C_6$–$C_{14}$ aryl, or an inorganic, alkyl ammonium or protonated amino acid cation;

R₂ is H, $C_1$–$C_{10}$ alkyl, $C_6$–$C_{14}$ aryl, optionally substituted —C O $C_6$–$C_{14}$ alkyl, optionally substituted —C S $C_6$–$C_{14}$ alkyl, optionally substituted —C O $C_6$–$C_{14}$ aryl, optionally substituted —C S $C_6$–$C_{14}$ aryl, or R₂ together with the sulfur to which it is attached form a thioester of a saturated or unsaturated fatty acid, lactic acid, retinoic acid or ascorbic acid; and R₃ is H, $C_1$–$C_{10}$ alkyl or $C_6$–$C_{14}$ aryl;

or a pharmaceutically acceptable salt thereof; thereby inhibiting matrix metalloproteinases in said chronic wound.

3. The method of claim 1, wherein the composition is in the form of an ointment for topical administration.

4. The method of claim 3, wherein the compound or salt thereof is from 0.001% to 10% w/v of the composition.

5. The method according to claim 1, wherein the composition is in the form of a solid ulcer dressing having the compound or salt thereof dispersed on or in the dressing.

6. A method for the treatment or prophylaxis of a chronic wound in a mammal, the chronic wound being selected from the group consisting of venous ulcers, diabetic ulcers, and pressure sores, the method comprising the step of topically applying to the chronic wound an effective amount of a composition comprising gluthathione or a pharmaceutically acceptable salt thereof, thereby inhibiting matrix metalloproteinases in said chronic wound.

7. A method for the treatment or prophylaxis of a chronic wound in mammals, the chronic wound being selected from the group consisting of venous ulcers, diabetic ulcers, and pressure sores, the method comprising the step of systemically administering an effective amount of a composition comprising gluthathione or a pharmaceutically acceptable salt thereof, thereby inhibiting matrix metalloproteinases in said chronic wound.

8. The method of claim 6 wherein the composition is in the form of an ointment for topical administration.

9. The method of claim 8, wherein the compound or salt thereof is from 0.001% to 10% w/v of the composition.

10. The method according to claim 6, wherein the composition is in the form of a solid ulcer dressing having the compound or salt thereof dispersed on or in the dressing.

11. A method for inhibiting matrix metalloproteinases for the treatment or prophylaxis of a chronic wound in a mammal, the chronic wound being selected from the group consisting of venous ulcers, diabetic ulcers, and pressure sores, the method comprising the step of topically applying to the chronic wound an effective amount of a composition comprising a compound of the formula:

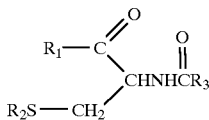

wherein:

R₁ is H, $C_1$–$C_{10}$ alkyl, $C_6$–$C_{14}$ aryl, or an inorganic, alkyl ammonium or protonated amino acid cation;

R₂ is H, $C_1$–$C_{10}$ alkyl, $C_6$–$C_{14}$ aryl, optionally substituted —C O $C_6$–$C_{14}$ alkyl, optionally substituted —C S $C_6$–$C_{14}$ alkyl, optionally substituted —C O $C_6$–$C_{14}$ aryl, optionally substituted —C S $C_6$–$C_{14}$ aryl, or R₂ together with the sulfur to which it is attached form a thioester of a saturated or unsaturated fatty acid, lactic acid, retinoic acid or ascorbic acid; and R₃ is H, $C_1$–$C_{10}$ alkyl or $C_6$–$C_{14}$ aryl;

or a pharmaceutically acceptable salt thereof; thereby inhibiting said matrix metalloproteinases in said chronic wound.

12. A method for inhibiting matrix metalloproteinases for the treatment or prophylaxis of a chronic wound in a mammal, the chronic wound being selected from the group consisting of venous ulcers, diabetic ulcers, and pressure sores, the method comprising the step of systemically administering an effective amount of a composition comprising a compound of the formula:

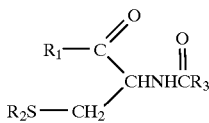

wherein:

R₁ is H, $C_1$–$C_{10}$ alkyl, $C_6$–$C_{14}$ aryl, or an inorganic, alkyl ammonium or protonated amino acid cation;

R₂ is H, $C_1$–$C_{10}$ alkyl, $C_6$–$C_{14}$ aryl, optionally substituted —C O $C_6$–$C_{14}$ alkyl, optionally substituted —C S $C_6$–$C_{14}$ alkyl, optionally substituted —C O $C_6$–$C_{14}$ aryl, optionally substituted —C S $C_6$–$C_{14}$ aryl, or R₂ together with the sulfur to which it is attached form a thioester of a saturated or unsaturated fatty acid, lactic acid, retinoic acid or ascorbic acid; and R₃ is H, $C_1$–$C_{10}$ alkyl or $C_6$–$C_{14}$ aryl;

or a pharmaceutically acceptable salt thereof; thereby inhibiting said matrix metalloproteinases in said chronic wound.

13. The method of claim 11, wherein the composition is in the form of an ointment for topical administration.

14. The method of claim 13, wherein the compound or salt thereof is from 0.001% to 10% w/v of the composition.

15. The method according to claim 11, wherein the composition is in the form of a solid ulcer dressing having the compound or salt thereof dispersed on or in the dressing.

16. A method for inhibiting matrix metalloproteinases for the treatment or prophylaxis of a chronic wound in a mammal, the chronic wound being selected from the group consisting of venous ulcers, diabetic ulcers, and pressure sores, the method comprising the step of topically applying to the chronic wound an effective amount of a composition comprising gluthathione or a pharmaceutically acceptable salt thereof, thereby inhibiting said matrix metalloproteinases in said chronic wound.

17. A method for inhibiting matrix metalloproteinases for the treatment or prophylaxis of a chronic wound in mammals, the chronic wound being selected from the group consisting of venous ulcers, diabetic ulcers, and pressure sores, the method comprising the step of systemically administering an effective amount of a composition comprising gluthathione or a pharmaceutically acceptable salt thereof, thereby inhibiting said matrix metalloproteinases in said chronic wound.

18. The method of claim 16 wherein the composition is in the form of an ointment for topical administration.

19. The method of claim 18, wherein the compound or salt thereof is from 0.001% to 10% w/v of the composition.

20. The method according to claim 16, wherein the composition is in the form of a solid ulcer dressing having the compound or salt thereof dispersed on or in the dressing.

* * * * *